(12) United States Patent
Jones

(10) Patent No.: US 6,383,133 B1
(45) Date of Patent: May 7, 2002

(54) OTOSCOPE KIT

(76) Inventor: Dwight T. Jones, 120 Forest St., Wellesley, MA (US) 02481

(*) Notice: Subject to any disclaimer, the term of this patent is extended or adjusted under 35 U.S.C. 154(b) by 0 days.

(21) Appl. No.: 09/436,151

(22) Filed: Nov. 9, 1999

(51) Int. Cl.$^7$ ................................................ A61B 1/227
(52) U.S. Cl. ...................................... 600/200; 600/184
(58) Field of Search ................................. 600/184, 200

(56) References Cited

U.S. PATENT DOCUMENTS

| | | | | |
|---|---|---|---|---|
| 765,887 A | * | 7/1904 | Geyerman | 600/200 |
| 1,686,041 A | * | 10/1928 | Smith | 600/200 |
| 3,038,466 A | * | 6/1962 | Moore | 600/184 |
| 3,146,775 A | * | 9/1964 | Moore et al. | 600/200 |
| 3,698,387 A | * | 10/1972 | Moore et al. | 600/200 |
| 3,870,036 A | * | 3/1975 | Fiore | 600/184 |
| 3,934,578 A | * | 1/1976 | Heine | 600/200 |
| 4,643,171 A | * | 2/1987 | Riester | 600/200 |
| 5,163,418 A | * | 11/1992 | Fraden et al. | 359/218 |
| 5,682,199 A | * | 10/1997 | Lankford | 348/72 |
| 5,879,289 A | * | 3/1999 | Yarush et al. | 600/179 |
| 5,916,150 A | * | 6/1999 | Sillman | 600/184 |
| 5,919,130 A | * | 7/1999 | Monroe et al. | 600/200 |
| 5,931,776 A | * | 8/1999 | Dotolo | 600/184 |
| 6,001,059 A | * | 12/1999 | Elliott | 600/184 |
| 6,074,405 A | * | 6/2000 | Koch | 606/160 |
| 6,152,873 A | * | 11/2000 | Rogers | 600/200 |
| 6,165,125 A | * | 12/2000 | Elliot | 600/200 |
| 6,190,310 B1 | * | 2/2001 | Cook | 600/200 |
| 6,213,938 B1 | * | 4/2001 | Cook | 600/200 |

FOREIGN PATENT DOCUMENTS

FR       2566668       *   1/1986   ................. 600/200

* cited by examiner

Primary Examiner—Nicholas D. Lucchesi
Assistant Examiner—Michael B. Priddy
(74) Attorney, Agent, or Firm—Iandiorio & Teska

(57) ABSTRACT

An otoscope kit includes a light source, an otoscope head for mounting on the light source; an adapter for removably mounting to the otoscope head, the adapter having a helical slit about its periphery; and at least one speculum for mounting on the adapter, the speculum having a projection wherein for engaging the slit for drawing the speculum into close contact with the adapter to removably secure the speculum to the adapter during use.

10 Claims, 2 Drawing Sheets

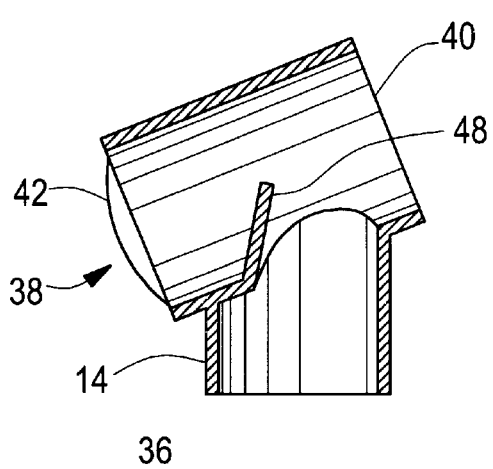
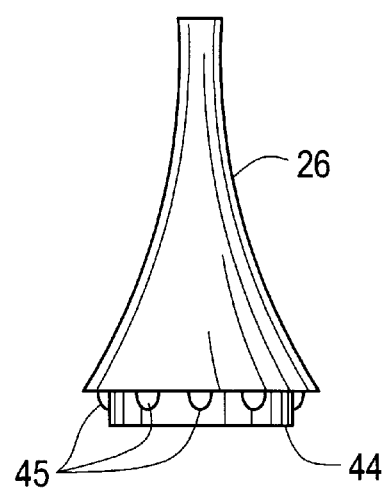
FIG. 2                FIG. 3
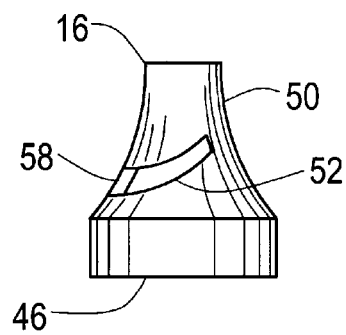
FIG. 4
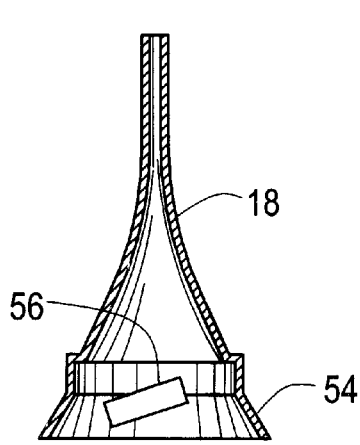
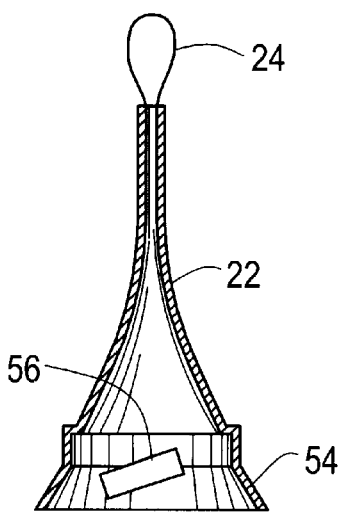
FIG. 5                FIG. 6

OTOSCOPE KIT

FIELD OF INVENTION

This invention relates to otoscopes, and more particularly to an otoscope kit which is water proof and easily sterilized.

BACKGROUND OF INVENTION

Otoscopes have changed little since their introduction over fifty years ago. An otoscope permits a medical professional to inspect a patient's eardrum and ear canal as well as the nasal passages. They have a power source, either batteries, or 110 volts down converted from the wall outlet. Most are battery powered. They include a light bulb, usually halogen or xenon. The light is channeled down a speculum that is placed on the scope to look into the ear canal via either a reflective mirror, or fiber optics. The viewer looks down the lighted ear canal through a magnified lens. Welch-Allyn and Heine are leaders in the field of otoscopes in the United States. All otoscopes use a plastic type of speculum that is placed on the otoscope and then inserted into the ear canal or nasal passage. The specula are either reusable, or disposable. Several specula attachments are known which permit the above examinations as well as specula which allow debris to be removed from the ear canal. While some devices may be sterilized to allow reuse on subsequent patients, the safest protection against transmitting disease and bacteria is to use disposable specula. While disposable specula exist as discussed above, these devices wear on some otoscope heads not designed for their use, resulting in poor fit and requiring replacement of the head. Moreover, standard otoscopes are not water proof and may fail in the field when exposured to water or bodily secretions. Further, current otoscopes are difficult to clean and sterilize, because they are not water proof, and because of their one piece construction. See U.S. Pat. No. 3,146,775.

BRIEF SUMMARY OF THE INVENTION

It is therefore an object of this invention to provide an otoscope kit which reduces and even eliminates the spread of disease.

It is a further object of this invention to provide such an otoscope kit which is easily sterilized to reduce the risk of the spread of disease.

It is a further object of this invention to provide such an otoscope kit which is adapted to use disposable specula.

It is a further object of this invention to provide such an otoscope kit which is lightweight and easily transportable.

It is a further object of this invention to provide such an otoscope kit which is cost effective to produce and implement.

The invention results from the realization that a truly waterproof, sterilizable otoscope kit includes an independent light source, a removable otoscope head for mounting onto the light source, and a removable adapter for attaching to the otoscope head a speculum which may be disposable or easily sterilized.

This invention features an otoscope kit including a light source, an otoscope head for mounting on the light source, an adapter for mounting on the otoscope head, the adapter having a helical slit about its periphery, and at least one speculum for mounting on the adapter, the speculae having a projection therein for engaging the slit to removably secure the speculae to the adapter during use.

In a preferred embodiment the speculum may be disposable. The speculum may include a loop at its distal end for removing debris from an ear canal. The kit may include a nasal exam head. The light source may be watertight.

BRIEF DESCRIPTION OF THE DRAWINGS

Other objects, features and advantages will occur to those skilled in the art from the following description of a preferred embodiment and the accompanying drawings, in which:

FIG. 2 is a cross sectional view of an otoscope head included in the kit according to the present invention;

FIG. 3 is a plan view of a reusable speculum which does not require an adapter;

FIG. 4 is a plan view of the adapter of the otoscope kit showing a helical slit according to the kit of the present invention;

FIG. 5 is a cross sectional view of a speculum which may be included in the kit showing a projection therein for engaging the helical slit of FIG. 4; and FIG. 6 is a cross sectional view of a looped speculum used to remove debris from an ear canal.

DISCLOSURE OF PREFERRED EMBODIMENT

Figure 1:
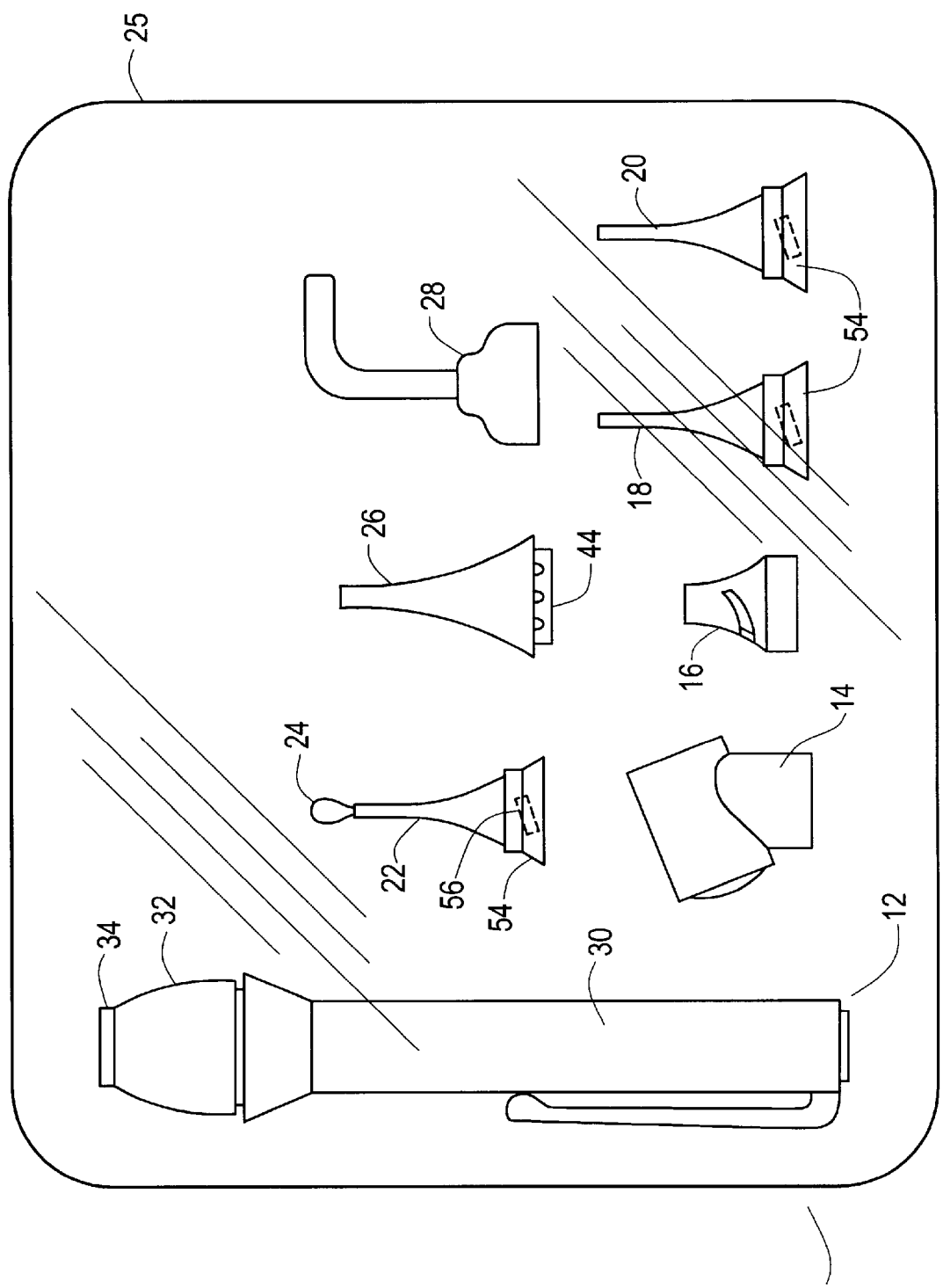
FIG. 1 is a schematic view of an otoscope kit according to the present invention.

Otoscope kit 10, FIG. 1, includes light source 12, otoscope head 14, cone shaped adapter 16 and at least one of reusable cone speculum 18 or disposable cone speculum 20. There may also be included disposable cone shaped speculum 22, including loop 24 for removing debris from the ear canal, reusable speculum 26, or reusable nasal examination head 28. The kit 10 may include container 25 for carrying kit 10 and may be, for example, a plastic case.

Light source 12 may be, for example, a 1900C. light such as is available from Pelian Products, Torrance, Calif., which is light weight and water tight, and of the type which is energized as body 30 is rotated with respect to light emitting end 32. Light emitting end 32 terminates in annular wall 34. Annular wall 34 receives otoscope head 14, FIG. 2, via base rim 36 to create a friction fit about annular wall 34 to removably mount otoscope head 14 onto light source 12 for easy cleaning and sterilization. Otoscope head 14 further includes viewing end 38 and attachment end 40. Viewing end 38 includes magnifying lens 42 allowing the user to better view the site being inspected. Attachment end 40 is provided to receive annular base rim 44, FIG. 3, of reusable speculum 26. Thus reusable speculum 26 may be removed for easy cleaning and sterilization. Annular base rim 44 may also include low profile projections 45 which provide a tighter friction fit between speculum 18 and attachment end 40.

Attachment end 40 also receives annular base 46, FIG. 4, of adapter 16. Annular base 46 forms friction fit within attachment end 40, FIG. 2. When light source 12 is energized, light from light source 12 is directed through speculum 26, or adapter 16, via mirror 48, FIG. 2, to illuminate the site to be examined.

Adapter 16, FIG. 4 includes cone portion 50 which includes helical slit 52 about the periphery of cone portion 50. Adapter 16 is provided for securing disposable specula 18 and 22, FIGS. 5 and 6, or reusable speculum 20, FIG. 1, via flared end 54. Specula 18, 20 and 22 include a projection 56 on the interior of flared end 54 for engaging helical slit 52 of adapter 16, FIG. 4. Projection 56 is canted in the same direction as helical slit 52 such that specula 18–20 are rotated clockwise, or counterclockwise depending on the direction of slit 52, projection 56 engages the slit, drawing flared end 54 into close contact with adapter 16 as projection 56 approaches slit stop 58, FIG. 3.

Loop 24, FIG. 6, is provided at the distal end of speculum 22 to permit the user to remove ear wax built-up or other debris from the ear canal to clear the ear canal. Speculum 22 may be reusable, or disposable, however given the type of use, disposability is preferred.

The advantage of adapter 16, of course, is that disposable specula 18 and 20, which have a cost of less than one cent, may be used. Moreover, specula 18-20 may be utilized without risk of wearing out attachment end 40 of otoscope head 14 extending the useful life of kit 10. Further, adapter 16, resusable specula 20, 26 and 28 may be easily removed for cleaning and sterilization, unlike the prior art, preventing the risk of transferring bacteria and other disease to subsequent patients and without risk of damaging the otoscope light source 12.

Although specific features of the invention are shown in some drawings and not in others, this is for convenience only as each feature may be combined with any or all of the other features in accordance with the invention.

Other embodiments will occur to those skilled in the art and are within the following claims:

What is claimed is:

1. An otoscope kit comprising;
   a light source having a first end and a second end;
   an otoscope head for mounting on said first end of said light source, such that light emitted from said light source is directed into said otoscope head;
   an adapter for mounting to the otoscope head, the adapter having a periphery including a helical slit about said periphery; and
   at least one speculum for mounting on the adapter, the speculum having a projection therein for engaging the slit for drawing the speculum into close contact with the adapter to removably secure the speculum to the adapter for use.

2. The otoscope kit of claim 1 in which the speculum is disposable.

3. The otoscope kit of claim 1 in which the speculum includes a loop at a distal end for removing debris from an ear canal.

4. The otoscope kit of claim 1 further including a nasal exam head.

5. The otoscope kit of claim 1 in which the light source is water tight.

6. An otoscope kit comprising:
   a light source having a first end and a second end, said light source including a lamp for directing light outwardly from said first end of said light source;
   an otoscope head for mounting on said first end of said light source, said otoscope head including an attachment end and a magnifying lens on an opposing end, and a mirror inside said otoscope head for directing light from said lamp through said attachment end;
   an adapter for mounting to said otoscope head at said attachment end, said adapter having a periphery and including a helical slit about said periphery; and
   at least one speculum for mounting on said adapter, said speculum having a projection therein for engaging said slit for drawing said speculum into close contact with said adapter to removably secure said speculum to said adapter for use.

7. The otoscope kit of claim 6 in which the speculum is disposable.

8. The otoscope kit of claim 6 in which the speculum includes a loop at a distal end for removing debris from an ear canal.

9. The otoscope kit of claim 6 further including a nasal exam head.

10. The otoscope kit of claim 6 in which the light source is water tight.

* * * * *